United States Patent [19]

Wade

[11] 4,198,422
[45] Apr. 15, 1980

[54] SUBSTITUTED 2,3-NAPHTHIMIDAZOLE CARBAMATES AND METHOD

[75] Inventor: Peter C. Wade, Pennington, N.J.

[73] Assignee: E. R. Squibb & Sons, Inc., Princeton, N.J.

[21] Appl. No.: 39,711

[22] Filed: May 17, 1979

[51] Int. Cl.² ............... A61K 31/415; C07D 235/32
[52] U.S. Cl. ............... 424/273 B; 260/578; 548/306
[58] Field of Search ............... 548/306; 424/273 B

[56] References Cited

U.S. PATENT DOCUMENTS

| Re. 28,403 | 4/1975 | Actor et al. | 548/306 |
|---|---|---|---|
| 3,929,821 | 12/1975 | Beard et al. | 548/306 |
| 4,002,640 | 1/1977 | Beard et al. | 548/306 |
| 4,046,908 | 9/1977 | Haugwitz et al. | 548/306 |
| 4,076,825 | 2/1978 | Haugwitz et al. | 424/273 B |
| 4,076,828 | 2/1978 | Haugwitz et al. | 424/273 B |
| 4,088,771 | 5/1978 | Roszkowski et al. | 548/315 |
| 4,110,463 | 8/1978 | Beard et al. | 548/315 |
| 4,129,661 | 12/1978 | Roszkowski et al. | 548/315 |

OTHER PUBLICATIONS

Brown Chem. Abst. 1958, vol. 52, col. 20134.

Primary Examiner—Natalie Trousof
Attorney, Agent, or Firm—Lawrence S. Levinson; Burton Rodney

[57] ABSTRACT

Substituted 2,3-naphthimidazole carbamates are provided having the structure

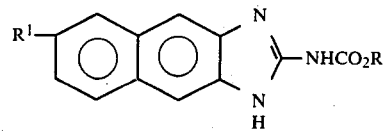

wherein R is lower alkyl, $R^1$ is hydrogen, halogen or

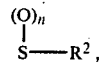

and $R^2$ is lower alkyl, $CH_2$-lower alkenyl, $CH_2$-lower alkynyl, phenyl or phenyl substituted with halogen, lower alkoxy, cyano, lower alkyl or trifluoromethyl, and n is 0, 1 or 2. These compounds are useful as anthelmintics.

In addition, intermediates and a method of use are also provided.

7 Claims, No Drawings

SUBSTITUTED 2,3-NAPHTHIMIDAZOLE CARBAMATES AND METHOD

DESCRIPTION OF THE INVENTION

The present invention relates to substituted 2,3-naphthimidazole carbamates having the structure

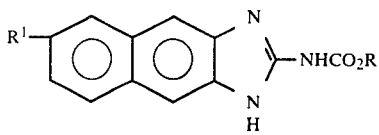

wherein R is lower alkyl, $R^1$ is hydrogen, halogen or

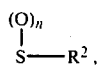

and $R^2$ is lower alkyl, $CH_2$-lower alkenyl, $CH_2$-lower alkynyl, phenyl or phenyl substituted with halogen, lower alkoxy, cyano, lower alkyl or trifluoromethyl, and n is 0, 1 or 2.

The term "lower alkyl" or "alkyl" as used herein whether employed as an independent substituent or as a part of another substituent includes straight or branched chain aliphatic hydrocarbon radicals having up to and including 7 carbon atoms, preferably 1 to 3 carbons, such as methyl, ethyl, propyl, isopropyl, butyl, isobutyl, t-butyl, amyl, hexyl, heptyl and the like.

The term "lower alkoxy" or "alkoxy" whether employed as an independent substituent or as a part of another substituent includes any of the above lower alkyl or alkyl groups linked to an oxygen atom.

The term "$CH_2$-lower alkenyl" refers to an unsaturated hydrocarbon group having from 3 to 6 carbon atoms and a single carbon-carbon double bond, linked to a methylene group. Typical —$CH_2$-lower alkenyl groups include, for example, 2-propenyl-$CH_2$—, 1-propenyl-$CH_2$—, 1-butenyl-$CH_2$—, 2-butenyl-$CH_2$—, 3-butenyl-$CH_2$—, and the like.

The term "$CH_2$-lower alkynyl" refers to an unsaturated hydrocarbon group having from 3 to 6 carbon atoms, and a single carbon-carbon triple bond, linked to a methylene group. Typical —$CH_2$-alkynyl groups include, for example, 1-propynyl-$CH_2$—, 1-butynyl-$CH_2$—, 2-propynyl-$CH_2$—, 2-butynyl-$CH_2$—, 3-butynyl-$CH_2$—, and the like.

The term "halogen" as used herein refers to chlorine, bromide, fluorine or iodine with bromine being preferred.

Preferred are those compounds wherein R is methyl or ethyl, $R^1$ is hydrogen, or $R^2$—S or

wherein $R^2$ is lower alkyl or phenyl.

Thus, the substituted 2,3-naphthimidazole carbamates of formula I include the following types:

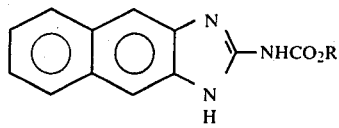

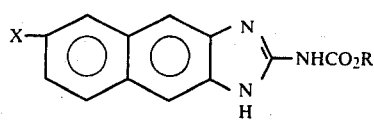

wherein X is halogen

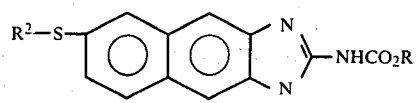

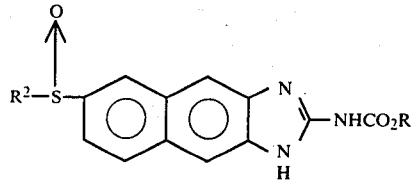

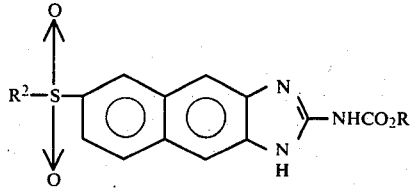

The compounds in accordance with the present invention may be prepared as follows.

The compounds of formula I wherein $R^1$ is hydrogen (formula II) may be prepared by reacting 2,3-naphthalenediamine with an isothiourea of the structure VII

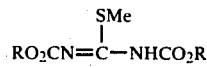

in the presence of an alcohol solvent (ROH) or other non-reacting solvent, and optionally, an acid catalyst, such as acetic acid at temperatures ranging from about 50° to about 200° C., and preferably from about 80° to about 130° C., for one minute to 72 hours, preferably for 1 to 24 hours.

The compounds of formula III of the invention, that is, wherein $R^1$ is halogen, may be prepared by forming a 2-amino-7-halo-3-nitronaphthalene of the structure VIII

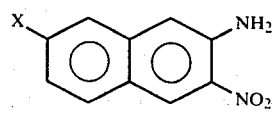

wherein X is halogen, reducing the formula VIII compound to the corresponding diamine IX employing conventional reduction techniques, for example, catalytically with hydrogen and platinum or chemically with dithionite, or zinc and acetic acid

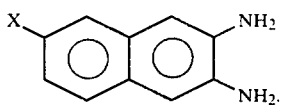

The diamine IX is a new intermediate and, as such, forms a part of the present invention.

The diamine IX may then be reacted with the isothiourea VII under the conditions described above with respect to the preparation of the formula II compounds, to form the formula III compounds of the invention.

The formula VIII compound is a new intermediate and may be prepared by the procedure of Curtis et al., J. Chem. Soc. 1959, 1670-6 using 2-amino-7-halo-naphthalene in place of 2-amino-naphthalene.

In an alternative procedure for preparing the formula VIII compound, the Curtis et al method is followed except that in the Curtis et al dehydrogenation step, the intermediate is reacted with palladium on charcoal and a hydrogen receptor such as cyclohexane.

Compounds of formula IV may be prepared as follows. The appropriate mercaptan of formula X

is dissolved in an alcohol solvent (ROH) in the presence of an alkali metal alkoxide, such as sodium methoxide; after evaporation, the residue is taken up in a non-reacting solvent, such as dimethylformamide or acetonitrile and this mixture is reacted with the 2-amino-7-halo-3-nitronaphthalene of formula VIII, preferably under reflux, to form the thionaphthalene compound of the structure XI

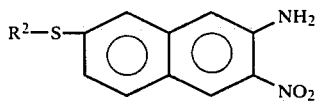

The intermediate XI is a new compound.

The formula XI compound is then reduced employing convention reduction techniques as described hereinbefore with respect to the preparation of the formula IX compound to form the diamine of formula XII

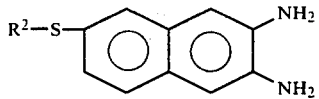

which is a new intermediate.

The formula XII diamine may then be cyclized to the formula IV compound of the invention by reaction with an isothiourea of formula VII employing conditions similar to that described with respect to the preparation of the formula II compound of the invention.

The formula IV compound may be oxidized to the corresponding sulfoxide V employing one equivalent of an oxidizing agent such as hydrogen peroxide in acetic acid, sodium meta periodate or m-chloroperbenzoic acid.

The sulfone of formula VI may be prepared by reacting the thio compound IV with two or more equivalents of any of the above oxidizing agents; alternatively, the sulfone VI may be prepared by reacting the sulfoxide V with one equivalent of any of the above oxidizing agents.

Compounds of structures V and VI may also be prepared by oxidizing the formula XI 2-amino-3-nitronaphthalene derivative with one or two or more equivalents of oxidizing agent to form a compound of the structure

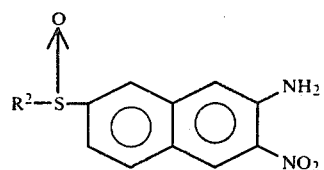

or

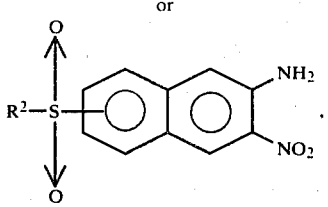

respectively, which is then reduced to the corresponding diamine XV or XVI.

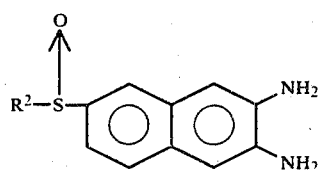

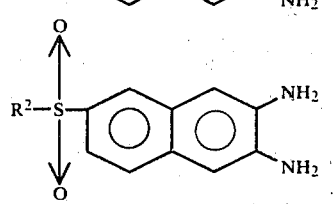

The diamine XV or XVI is then reacted with the isothiourea VII in the presence of an alcohol solvent (ROH) or other non-reacting solvent to form the compound of structure V or VI.

The compounds of structures XIII, XIV, XV and XVI are new intermediates.

The starting materials employed in the above reactions are either known in the art or easily prepared according to conventional techniques.

The various novel intermediates of the invention may be defined by the structure

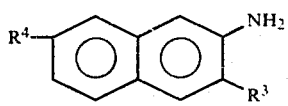

wherein $R^3$ is $NH_2$ or $NO_2$ and $R^4$ is halogen or

wherein $R^2$ is lower alkyl, $CH_2$-lower alkenyl, $CH_2$-lower alkynyl, phenyl, or phenyl substituted with halogen, lower alkoxy, cyano, lower alkyl or trifluoromethyl, and n is 0, 1 or 2.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

The compounds of formula I have anthelmintic activity and are useful in the treatment and/or prevention of helminthiasis, a parasitic disease which causes widespread and often serious infection in domesticated animals such as swine, horses, cattle, dogs, cats and sheep. The compounds are useful in treating infections caused by Haemonchus, Ostertagia, Trichostrongylus, Cooperia, Dictyocaulus, Nematodirus, Bunostomum, Strongyloides, Oesophagostomum, Trichuris, Moniezia, and liver flukes (for example in sheep). In treating domesticated animals, the compounds are given orally; however, other routes such as parenterally, for example, subcutaneously, intravenously, interperitoneally and intramuscularly may be employed.

Where the compounds are administered orally, they may be mixed with a nontoxic, edible carrier to form a feed supplement, or be administered in unit dosage forms such as powders, capsule, tablet, boluses, drenches, etc.

Where the compounds are administered parenterally, they may be dispersed (for example, suspended) in non-toxic non-pyrogenic physiologically acceptable carriers such as water, benzyl benzoate, 1,3-butylene glycol, ethyl oleate, glyceryl triacetate, castor oil, sesame oil, and sesame oil:benzyl benzoate (1:1). The parenteral product will usually take the form of a suspension containing from about 1 to about 10% by weight of the compound of formula I in anyone or mixture of the above carriers.

In general, the compounds of formula I exhibit anthelmintic activity when administered to animals (parenterally or orally) in a single dose of about 1 to about 100 mg per kilogram of animal body weight. It is preferred to employ in the range of 2.5–100 mg per kilogram of body weight. The compounds may be divided into a plurality of smaller doses given parenterally or orally over one or more days.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%. Lastly, feeds containing the active ingredient may be made directly by mixing said active ingredient in a feed which is inert to said anthelmintic compounds so as to give feeds having concentrations of anthelmintic agent of from 0.1–2%.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

(1H-Naphth[2,3-c]imidazol-2-yl)carbamic acid, methyl ester

A. 1,3-Bis(methoxycarbonyl)-S-methyl-isothiourea

To a solution of 11.2 g of 2-methyl-2-thiopseudourea sulfate in 200 ml of water at 0° C. there is added concurrently 260 ml of 25% NaOH and 160 ml of methylchloroformate at such a rate that the pH remains between 7 and 8 as monitored by a pH meter. After the addition is complete the mixture is stirred for an additional 2 hours at room temperature. Then 400 ml of water is added and the mixture is extracted with dichloromethane. The organic layers are combined, dried over magnesium sulfate, and evaporated in vacuo to give a white solid. Crystallization from methanol yields 60.4 g of the title A compound, m.p. 99°–101° C.

B. (1H-Naphth[2,3-c]imidazol-2-yl)-carbamic acid, methyl ester

A mixture of 2.5 g (0.0158 mol) of 2,3-naphthalenediamine, 3.3 g of 1,3-bis[methoxycarbonyl]-S-methyl-isothiourea, 8 drops of acetic acid and 100 ml of methanol is refluxed for 2 hours. The resulting precipitate is filtered off, recrystallized from acetic acid then digested with a small amount of acetic acid for 2 hours. The resulting material is dried overnight at 40° then for 2 hours at 100° (1 torr) to yield 1.6 g (42%) of the title product: m.p. >300°.

EXAMPLE 2

2-Amino-7-chloro-3-nitronaphthalene

A. 2-Acetamido-7-chloro naphthalene (150 g) is suspended in 250 ml of decalin and hydrogenated at 800 psi between 175° and 200° for 30 minutes with Raney nickel W-2. The reaction mixture is filtered. The decalin is removed under vacuum and the product is purified by chromatography on silica gel. 7.5 g of the resulting tetrahydronaphthalene in 30 ml of acetic acid is nitrated by the dropwise addition of a mixture of 3.5 ml of nitric acid (d=1.4) and 2.5 ml of sulfuric acid (d=1.4). The temperature is kept below 45°. After 30 minutes the mixture is poured into ice water and stirred. The product is filtered off and recrystallized from 95% ethanol. The 6-acetamido-2-chloro-7-nitro-1,2,3,4-tetrahydronaphthalene thus obtained (20 g from several combined nitrations), N-bromosuccinimide (32 g) and benzoyl peroxide (0.5 g) in 200 ml carbon tetrachloride are heated to reflux with a 250 watt infrared lamp—the lamp and flask being enclosed in aluminum foil. After the initial vigorous reaction, the reaction is heated for a further 20 minutes. The mixture is concentrated to 100 ml in a nitrogen stream and cooled to 0°. The dibromo compound is isolated by crystallization from ethanol or chromatography on silica gel.

The dibromo compound obtained above (16 g) is added rapidly to a boiling solution of potassium acetate (fused, 15 g) in 150 ml of dry methanol and the solution boiled for 5 minutes. The mixture is poured into 2 liters of ice water and the mono-bromo product filtered off and recrystallized from methanol or chromatographed on silica gel.

The mono-bromo compound 13 g is boiled for 1 hour in a mixture of 100 ml of ethanol, 50 ml of hydrochloric acid (d=1.2) and 10 ml of water. The mixture is poured into an excess of dilute aqueous ammonia. After standing at 0° the 2-amino 7-chloro-3-nitronaphthalene crystallizes out.

B. In an alternative procedure the 6-amino-2-chloro-7-nitro-1,2,3,4-tetrahydronaphthalene (5 g) prepared above in part A is boiled in 100 ml of cyclohexene with 1 g of 10% Pd/C for 2 hours. The catalyst is filtered off and the volatiles removed under vacuum. The product is isolated by crystallization from methanol or chromatography on silica gel. The acetyl group is removed by hydrolysis as above.

EXAMPLE 3

7-Chloro-2,3-naphthalenediamine

To 0.025 mole of the 2-amino-7-chloro-3-nitronaphthalene (prepared in Example 2) in 100 ml of 95% ethanol is added a solution of 3.4 equivalents of sodium hydrosulfite ($Na_2S_2O_4$) in a solution of 100 ml of water and 15 ml concentrated (28%) ammonium hydroxide. The mixture is refluxed for 5 minutes and an amount of hydrosulfite solution equal to 10% of the original is added to the relfuxing mixture. TLC (silica gel, ether) indicates consumption of starting material. The mixture is concentrated to one-half its original volume under vacuum and the residual mixture extracted with two 150 ml portions of chloroform. The combined chloroform extracts are dried ($Na_2SO_4$), filtered, and evaporated to dryness to yield the crude title compound which is used without further purification in Example 4.

EXAMPLE 4

[7-Chloro(1H-naphth[2,3-c]imidazol-2yl)]carbamic acid, methyl ester

A mixture of 0.0158 mol of 7-chloro-2,3-naphthalenediamine, 3.3 g of 1,3-bis[methoxycarbonyl]-S-methyl-isothiourea, 8 drops of acetic acid and 100 ml of methanol is refluxed for 2 hours. The resulting precipitate is filtered off, recrystallized from acetic acid, then digested with a small amount of acetic acid for 2 hours. The resulting material is dried overnight at 40° then for 2 hours at 100° (1 torr) to yield the title product.

EXAMPLE 5

2-Amino-7-isobutylthio-3-nitronaphthalene

To 1 mole of isobutylmercaptan in 500 ml of methanol stirring at room temperature is added 1.1 mol of sodium methoxide. The mixture is stirred for 10 minutes and the solvent is evaporated under vacuum. The residue is taken up in 500 ml of dimethylformamide. To this mixture, stirring at room temperature, is added 1 mole of 2-amino-7-chloro-3-nitronaphthalene. The mixture is refluxed for 2 hours, then cooled and poured into 2 liters of water. After stirring for 30 minutes the resulting precipitate is filtered off and recrystallized from methanol or ethanol to yield the title compound.

EXAMPLE 6

7-Isobutylthio-2,3-naphthalenediamine

To 0.025 mole of the 2-amino-7-isobutylthio-3-nitronaphthalene (prepared in Example 5) in 100 ml of 95% ethanol is added a solution of 3.4 equivalents of sodium hydrosulfite ($Na_2S_2O_4$) in a solution of 100 ml of water and 15 ml concentrated (28%) ammonium hydroxide. The mixture is refluxed for 5 minutes and an amount of hydrosulfite solution equal to 10% of the original is added to the refluxing mixture. TLC (silica gel, ether) indicates consumption of starting material. The mixture is concentrated to one-half its original volume under vacuum and the residual mixture extracted with two 150 ml portions of chloroform. The combined chloroform extracts are dried ($Na_2SO_4$), filtered, and evaporated to dryness to yield the crude title compound which is used without further purification in Example 7.

EXAMPLE 7

[7-Isobutylthio(1H-naphth[2,3-c]imidazol-2-yl)]carbamic acid, methyl ester

A mixture of 0.0158 mol of 7-isobutylthio-2,3-naphthalenediamine, 3.3 g of 1,3-bis-[methoxycarbonyl]-S-methyl-isothiourea, 8 drops of acetic acid and 100 ml of methanol is refluxed for 2 hours. The resulting precipitate is filtered off, recrystallized from acetic acid then digested with a small amount of acetic acid, for 2 hours. The resulting material is dried overnight at 40°, then for 2 hours at 100° (1 torr) to yield the title product.

EXAMPLE 8

2-Amino-7-isobutylsulfinyl-3-nitronaphthalene

To 0.1 mol of 2-amino-7-isobutylthio-3-nitronaphthalene, prepared in Example 5, stirring in 200 ml of chloroform at 4°-6° (ice bath), is added 0.1 mol of m-chloroperbenzoic acid in 160 ml of chloroform over 3 hours. Consumption of starting material is confirmed by TLC (silica gel, ether). The reaction mixture is washed 3 times with saturated $NaHCO_3$ solution, dried ($Na_2SO_4$), and filtered. The filtrate is evaporated to dryness under vacuum and the residue recrystallized from ethanol (absolute) to yield the title compound.

EXAMPLE 9

7-Isobutylsulfinyl-2,3-naphthalenediamine

To 0.025 mole of the 2-amino-7-isobutylsulfinyl-3-nitronaphthalene in 100 ml of 95% ethanol is added a solution of 3.4 equivalents of sodium hydrosulfite ($Na_2S_2O_4$) in a solution of 100 ml of water and 15 ml concentrated (28%) ammonium hydroxide. The mixture is refluxed for 5 minutes and an amount of hydrosulfite solution equal to 10% of the original is added to the refluxing mixture. TLC (silica gel, ether) indicates consumption of starting material. The mixture is concentrated to one-half its original volume under vacuum and the residual mixture extracted with two 150 ml portions of chloroform. The combined chloroform extracts are dried ($Na_2SO_4$), filtered, and evaporated to dryness to yield the crude title compound which is used without further purification in Example 10.

EXAMPLE 10

[7-Isobutylsulfinyl(1H-naphth[2,3-c]imidazol-2-yl)]-carbamic acid, methyl ester

A mixture of 0.0158 mol of 7-isobutylsulfinyl-2,3-naphthalenediamine, 3.3 g of 1,3-bis[methoxycarbonyl]-S-methyl-isothiourea, 8 drops of acetic acid and 100 ml of methanol is refluxed for 2 hours. The resulting precipitate is filtered off, recrystallized from acetic acid, then digested with a small amount of acetic acid for 2 hours. The resulting material is dried overnight at 40°, then for 2 hours at 100° (1 torr) to yield the title product.

EXAMPLE 11

2-Amino-7-isobutylsulfonyl-3-nitronaphthalene

To 0.1 mol of 2-amino-7-isobutylthio-3-nitronaphthalene, prepared in Example 5, stirring in 200 ml of chloroform at 4°-6° (ice bath) is added 0.2 mol of m-chloroperbenzoic acid in 160 ml of chloroform over 3 hours. Consumption of starting material is confirmed by TLC (silica gel, ether). The reaction mixture is washed 3 times with saturated NaHCO₃ solution, dried (Na₂SO₄), and filtered. The filtrate is evaporated to dryness under vacuum and the residue recrystallized from ethanol (absolute) to yield the title compound.

EXAMPLE 12

7-Isobutylsulfonyl-2,3-naphthalenediamine

To 0.025 mole of the 2-amino-7-isobutylsulfonyl-3-nitronaphthalene (prepared in Example 11) in 100 ml of 95% ethanol is added a solution of 3.4 equivalents of sodium hydrosulfite (Na₂S₂O₄) in a solution of 100 ml of water and 15 ml concentrated (28%) ammonium hydroxide. The mixture is refluxed for 5 minutes and an amount of hydrosulfite solution equal to 10% of the original is added to the refluxing mixture. TLC (silica gel, ether) indicates consumption of starting material. The mixture is concentrated to one-half its original volume under vacuum and the residual mixture extracted with two 150 ml portions of chloroform. The combined chloroform extracts are dried (Na₂SO₄), filtered, and evaporated to dryness to yield the crude title compound which is used without further purification in Example 13.

EXAMPLE 13

[7-Isobutylsulfonyl(1H-naphth[2,3-c]imidazol-2-yl)]-carbamic acid, methyl ester

A mixture of 0.0158 mol of 7-isobutylsulfonyl-2,3-naphthalenediamine, 3.3 g of 1,3-bis-[methoxycarbonyl]-S-methyl-isothiourea, 8 drops of acetic acid and 100 ml of methanol is refluxed for 2 hours. The resulting precipitate is filtered off, recrystallized from acetic acid, then digested with a small amount of acetic acid for 2 hours. The resulting material is dried overnight at 40°, then for 2 hours at 100° (1 torr) to yield the title product.

EXAMPLES 14 to 16

Following the procedure of Example 1 except substituting for 1,3-bis[methoxycarbonyl]-S-methylisothiourea, the isothiourea shown in Column I of Table A below, the product shown in Column II is obtained.

TABLE A

| Ex. No. | Column I<br>RO₂CN=C(SMe)—NHCO₂R<br>R | Column II<br>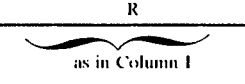<br>R |
|---|---|---|
| 14. | C₂H₅ | as in Column I |
| 15. | i-C₃H₇ | |
| 16. | n-C₄H₉ | |

EXAMPLES 17 to 21

Following the procedure of Examples 2, 3 and 4 except substituting the compound shown in Column I of Table B below for 2-acetamido-7-chloro-3-nitronaphthalene in Example 2, substituting the isothiourea shown in Column II for that used in Example 4, the intermediates and final product shown in Columns III, IV and V are obtained.

TABLE B

| Column I<br>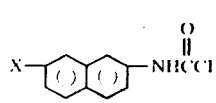<br>X | Column II<br>RO₂CN=C(SMe)—NHCO₂R<br>R | Column III<br><br>X | Column IV<br>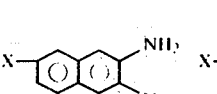<br>X | Column V<br>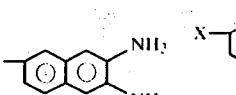<br>X | R |
|---|---|---|---|---|---|
| 17. Cl | C₂H₅ | as in Column I | as in Column I | as in Column I | as in Column II |
| 18. Br | CH₃ | | | | |
| 19. F | CH₃ | | | | |
| 20. Cl | n-C₃H₇ | | | | |
| 21. Br | n-C₄H₉ | | | | |

EXAMPLES 22 to 33

Following the procedure of Examples 5, 6 and 7 except substituting for isobutylmercaptan in Example 2 the compound shown in Column I of Table C set out below, and substituting the isothiourea shown in Column II for that used in Example 7, the intermediates and final products shown in Columns III, IV and V are obtained.

TABLE C

| | Column I | Column II | Column III | Column IV | Column V | |
|---|---|---|---|---|---|---|
| | | SMe<br>\|<br>$RO_2CN{=}C{-}NHCO_2R$ | $R^2{-}S{-}$⬡⬡$\begin{array}{c}NH_2\\NO_2\end{array}$ | $R^2{-}S{-}$⬡⬡$\begin{array}{c}NH_2\\NH_2\end{array}$ | $R^2{-}S{-}$⬡⬡$\diagup\!\!\!\diagdown\begin{array}{c}N\\\phantom{x}\\N\\H\end{array}\!\!\!\!NHCO_2R$ | |
| Ex. No. | $R^2{-}SH$<br>$R^2$ | R | $R^2$ | $R^2$ | $R^2$ | R |
| 22. | $CH_3$ | $CH_3$ | as in Column I | as in Column I | as in Column I | as in Column II |
| 23. | $C_2H_5$ | $C_2H_5$ | | | | |
| 24. | $CH_2{=}CH{-}CH_2$ | $CH_3$ | | | | |
| 25. | $CH_3CH{=}CH{-}CH_2$ | $CH_3$ | | | | |
| 26. | $CH{\equiv}C{-}CH_2$ | $C_2H_5$ | | | | |
| 27. | $CH_3C{\equiv}C{-}CH_2$ | $CH_3$ | | | | |
| 28. | $C_6H_5$ | $CH_3$ | | | | |
| 29. | $p{-}CH_3{-}C_6H_4{-}$ | $C_2H_5$ | | | | |
| 30. | $p{-}CH_3O{-}C_6H_4{-}$ | $CH_3$ | | | | |
| 31. | $m{-}CN{-}C_6H_4{-}$ | $CH_3$ | | | | |
| 32. | $p{-}Cl{-}C_6H_4{-}$ | $C_2H_5$ | | | | |
| 33. | $o{-}CF_3{-}C_6H_4{-}$ | $CH_3$ | | | | |

EXAMPLES 34 to 45

2,3-naphthimidazoles shown in Column IV of Table D are obtained.

TABLE D

| | Column I | Column II | Column III | | Column IV | | |
|---|---|---|---|---|---|---|---|
| Ex. No. | $R^2{-}S{-}$⬡⬡$\begin{array}{c}NH_2\\NO_2\end{array}$<br>$R^2$ | $R^2{-}S(\!\uparrow\!O)\!{-}$⬡⬡$\begin{array}{c}NH_2\\NO_2\end{array}$<br>$R^2$ | Ex. No. | $R^2{-}S(\!\uparrow\!O)\!{-}$⬡⬡$\begin{array}{c}NH_2\\NH_2\end{array}$<br>$R^2$ | Ex. No. | $R^2{-}S(\!\uparrow\!O)\!{-}$⬡⬡$\diagup\!\!\!\diagdown\begin{array}{c}N\\\phantom{x}\\N\\H\end{array}\!\!\!\!NHCO_2R$<br>R | $R^2$ |
| 34. | $CH_3$ | as in Column I | 46. | as in Column I | 58. | as in Column II of Table C | as in Column I |
| 35. | $C_2H_5$ | | 47. | | 59. | | |
| 36. | $CH_2{=}CH{-}CH_2$ | | 48. | | 60. | | |
| 37. | $CH_3CH{=}CH{-}CH_2$ | | 49. | | 61. | | |
| 38. | $CH{\equiv}C{-}CH_2$ | | 50. | | 62. | | |
| 39. | $CH_3C{\equiv}C{-}CH_2$ | | 51. | | 63. | | |
| 40. | $C_6H_5$ | | 52. | | 64. | | |
| 41. | $p{-}CH_3{-}C_6H_4{-}$ | | 53. | | 65. | | |
| 42. | $p{-}NO_2{-}C_6H_4{-}$ | | 54. | | 66. | | |
| 43. | $m{-}CN{-}C_6H_4{-}$ | | 55. | | 67. | | |
| 44. | $p{-}Cl{-}C_6H_4$ | | 56. | | 68. | | |
| 45. | $o{-}CF_3{-}C_6H_4{-}$ | | 57. | | 69. | | |

Following the procedure of Example 8, except substituting the 7-substituted thio-2-amino-3-nitronaphthalene compound shown in Column III of Table C (now Column I of Table D), for the 7-isobutylthio-2-amino-3-nitronaphthalene, the corresponding 7-substituted-sulfinyl-2-amino-3-nitronaphthalenes shown in Column II of Table D are obtained.

EXAMPLES 46 to 57

Following the procedure of Example 9, except substituting the 7-substituted-sulfinyl-2-amino-3-nitronaphthalenes of Examples 34 to 45 for the 7-isobutylsulfinyl-2-amino-3-nitronaphthalene, the corresponding 7-substituted-sulfinyl-2,3-naphthalenediamines shown in Column III of Table D are obtained.

EXAMPLES 58 to 69

Following the procedure of Example 10, except substituting the 7-substituted sulfinyl-2,3-naphthalenediamines of Examples 46 to 57 shown in Column III of Table D for the 7-isobutyl-sulfinyl2,3-naphthalenediamine and substituting the isothiourea shown in Column II of Table C, the sulfoxides of the 7-substituted thio-2,3-naphthimidazoles shown in Column IV of Table D are obtained.

EXAMPLES 70 to 81

Following the procedure of Example 11 except substituting the 7-substituted thio-2-amino-3-nitronaphthalene compound shown in Column III of Table C (now Column I of Table E), for the 7-isobutylthio-2-amino-3-nitronaphthalene, the corresponding 7-substituted-sulfonyl-2-amino-3-nitronaphthalene shown in Column II of Table E are obtained.

EXAMPLES 82 to 93

Following the procedure of Example 12, except substituting the 7-substituted-sulfonyl-2-amino-3-nitronaphthalenes of Examples 70 to 81 for the 7-isobutylsulfonyl-2-amino-3-nitronaphthalene, the corresponding 7-substituted-sulfonyl-2,3-naphthalenediamines are obtained.

EXAMPLES 94 to 105

Following the procedure of Example 13, except substituting the 7-substituted sulfonyl-2,3-naphthalenediamines of Examples 82 to 93 shown in Column III of Table E for the 7-isobutylsulfonyl2,3-naphthalenediamine and substituting the isothiourea shown in Column II of Table C, the sulfones of the 7-substituted thio-2,3-naphthimidazoles shown in Column IV of Table E are obtained.

2. The compound as defined in claim 1 wherein $R^1$ is hydrogen.

3. The compound as defined in claim 1 wherein $R^1$ is halogen.

4. The compound as defined in claim 1 wherein $R^1$ is $S-R^2$,

TABLE E

| Column I | | Column II | | Column III | | Column IV | |
|---|---|---|---|---|---|---|---|
| Ex. No. | $R^2$ | Ex. No. | $R^2$ | Ex. No. | $R^2$ | Ex. No. | R | $R^2$ |
| 70. | $CH_3$ | | as in Column I | 82. | as in Column I | 94. | as in Column II of Table C | as in Column I |
| 71. | $C_2H_5$ | | | 83. | | 95. | | |
| 72. | $CH_2=CH-CH_2$ | | | 84. | | 96. | | |
| 73. | $CH_3CH=CH-CH_2$ | | | 85. | | 97. | | |
| 74. | $CH\equiv C-CH_2$ | | | 86. | | 98. | | |
| 75. | $CH_3C\equiv C-CH_2$ | | | 87. | | 99. | | |
| 76. | $C_6H_5$ | | | 88. | | 100. | | |
| 77. | $p-CH_3-C_6H_4-$ | | | 89. | | 101. | | |
| 78. | $p-NO_2-C_6H_4-$ | | | 90. | | 102. | | |
| 79. | $m-CN-C_6H_4-$ | | | 91. | | 103. | | |
| 80. | $p-Cl-C_6H_4-$ | | | 92. | | 104. | | |
| 81. | $o-CF_3-C_6H_4-$ | | | 93. | | 105. | | |

What is claimed is:

1. A compound of the structure

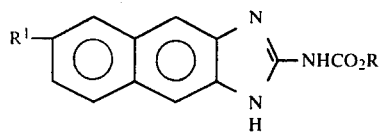

wherein R is lower alkyl, $R^1$ is hydrogen, halogen, or

wherein $R^2$ is lower alkyl, $CH_2$-lower alkenyl, $CH_2$-lower alkynyl, phenyl or phenyl substituted with halogen, lower alkoxy, cyano, lower alkyl or trifluoromethyl, and n is 0, 1 or 2, and pharmaceutically acceptable salts thereof.

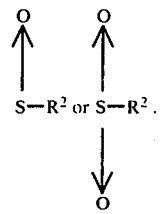

5. The compound as defined in claim 1 having the name (1H-naphth[2,3-c]imidazol-2-yl)-carbamic acid, methyl ester.

6. An anthelmintic composition comprising an effective amount of a compound as defined in claim 1, and a pharmaceutically acceptable carrier therefor.

7. A method for treating helminthiasis which comprises administering to a mammalian host an effective amount of the composition as defined in claim 6.

* * * * *

UNITED STATES PATENT AND TRADEMARK OFFICE
CERTIFICATE OF CORRECTION

PATENT NO. : 4,198,422
DATED : April 15, 1980
INVENTOR(S) : Peter C. Wade

It is certified that error appears in the above-identified patent and that said Letters Patent are hereby corrected as shown below:

Column 1, next to the first structure insert --I--.

Signed and Sealed this

Twelfth Day of August 1980

[SEAL]

Attest:

SIDNEY A. DIAMOND

Attesting Officer

Commissioner of Patents and Trademarks